United States Patent
Brockway et al.

(10) Patent No.: US 9,314,181 B2
(45) Date of Patent: Apr. 19, 2016

(54) METHOD AND APPARATUS FOR DETECTION OF HEARTBEAT CHARACTERISTICS

(71) Applicant: VivaQuant LLC, St. Paul, MN (US)

(72) Inventors: Marina Brockway, St. Paul, MN (US); Brian Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 0 days.

(21) Appl. No.: 14/630,918

(22) Filed: Feb. 25, 2015

(65) Prior Publication Data

US 2015/0164355 A1 Jun. 18, 2015

Related U.S. Application Data

(63) Continuation-in-part of application No. 14/230,439, filed on Mar. 31, 2014, now Pat. No. 9,072,438, and a (Continued)

(51) Int. Cl.

| | |
|---|---|
| *A61B 5/04* | (2006.01) |
| *A61B 5/046* | (2006.01) |
| *A61B 5/024* | (2006.01) |
| *A61B 5/021* | (2006.01) |
| *A61B 5/11* | (2006.01) |
| *A61B 5/026* | (2006.01) |
| *A61B 7/02* | (2006.01) |
| *A61B 7/00* | (2006.01) |

(Continued)

(52) U.S. Cl.
CPC ............ *A61B 5/046* (2013.01); *A61B 5/0006* (2013.01); *A61B 5/021* (2013.01); *A61B 5/026* (2013.01); *A61B 5/0245* (2013.01); *A61B 5/02416* (2013.01); *A61B 5/04014* (2013.01); *A61B 5/04017* (2013.01); *A61B 5/0452* (2013.01); *A61B 5/04087* (2013.01); *A61B 5/1102* (2013.01); *A61B 7/00* (2013.01); *A61B 7/02* (2013.01); *G06F 17/14* (2013.01); *G06K 9/0051* (2013.01); *G06K 9/0053* (2013.01); *A61B 5/7253* (2013.01); *G06F 19/3431* (2013.01)

(58) Field of Classification Search
None
See application file for complete search history.

(56) References Cited

U.S. PATENT DOCUMENTS

| | | |
|---|---|---|
| 5,090,418 A | 2/1992 | Squires et al. |
| 5,279,283 A | 1/1994 | Dillon |

(Continued)

FOREIGN PATENT DOCUMENTS

WO 2013/043157 A2 3/2013

OTHER PUBLICATIONS

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

(Continued)

*Primary Examiner* — Brian T Gedeon
(74) *Attorney, Agent, or Firm* — Crawford Maunu PLLC

(57) ABSTRACT

Aspects of the present disclosure are directed to detecting Atrial Fibrillation (AF). As may be implemented in accordance with one or more embodiments, a time series of interbeat intervals is computed from a recording of activity of a beating heart. The time series is decomposed into subcomponents, and an envelope of at least one of the subcomponents is computed. The presence of atrial fibrillation (AF) is detected based upon characteristics of the envelope that are indicative of AF.

31 Claims, 6 Drawing Sheets

Related U.S. Application Data continuation of application No. 13/668,898, filed on Nov. 5, 2012, now Pat. No. 8,688,202, which is a continuation-in-part of application No. PCT/US2011/052371, filed on Sep. 20, 2011, and a continuation-in-part of application No. 12/938,995, filed on Nov. 3, 2010, now Pat. No. 8,632,465, said application No. 13/668,898 is a continuation-in-part of application No. 13/172,415, filed on Jun. 29, 2011, now Pat. No. 8,433,395.

(60) Provisional application No. 61/944,253, filed on Feb. 25, 2014, provisional application No. 61/257,718, filed on Nov. 3, 2009, provisional application No. 61/366,052, filed on Jul. 20, 2010, provisional application No. 61/359,462, filed on Jun. 29, 2010, provisional application No. 61/370,026, filed on Aug. 2, 2010, provisional application No. 61/555,165, filed on Nov. 3, 2011.

(51) Int. Cl.

| | |
|---|---|
| A61B 5/00 | (2006.01) |
| A61B 5/0245 | (2006.01) |
| A61B 5/0408 | (2006.01) |
| A61B 5/0452 | (2006.01) |
| G06F 17/14 | (2006.01) |
| G06K 9/00 | (2006.01) |
| G06F 19/00 | (2011.01) |

(56) References Cited

U.S. PATENT DOCUMENTS

| | | | |
|---|---|---|---|
| 5,521,851 | A | 5/1996 | Wei et al. |
| 5,792,065 | A | 8/1998 | Xue et al. |
| 5,817,027 | A | 10/1998 | Arand et al. |
| 5,827,195 | A | 10/1998 | Lander |
| 5,987,352 | A | 11/1999 | Klein et al. |
| 6,389,308 | B1 | 5/2002 | Shusterman |
| 6,589,189 | B2 | 7/2003 | Meyerson et al. |
| 6,690,959 | B2 | 2/2004 | Thompson |
| 6,701,170 | B2 | 3/2004 | Stetson |
| 6,775,571 | B1 | 8/2004 | Kroll |
| 6,822,564 | B2 | 11/2004 | Al-Ali |
| 7,096,060 | B2 | 8/2006 | Arand et al. |
| 7,115,096 | B2 | 10/2006 | Siejko et al. |
| 7,236,819 | B2 | 6/2007 | Brockway et al. |
| 7,272,265 | B2 | 9/2007 | Kouri et al. |
| 7,376,453 | B1 | 5/2008 | Diab et al. |
| 7,480,529 | B2 | 1/2009 | Li |
| 7,627,369 | B2 | 12/2009 | Hunt |
| 7,672,717 | B1 | 3/2010 | Zikov et al. |
| 7,840,259 | B2 | 11/2010 | Xue et al. |
| 7,846,104 | B2 | 12/2010 | MacQuarrie et al. |
| 8,086,304 | B2 | 12/2011 | Brockway et al. |
| 8,201,330 | B1 | 6/2012 | Rood et al. |
| 8,214,007 | B2 | 7/2012 | Baker et al. |
| 8,271,073 | B2 | 9/2012 | Zhang et al. |
| 8,348,852 | B2 | 1/2013 | Bauer et al. |
| 8,460,189 | B2 | 6/2013 | Libbus et al. |
| 8,478,389 | B1 | 7/2013 | Brockway et al. |
| 8,588,908 | B2 | 11/2013 | Moorman et al. |
| 8,755,876 | B2 | 6/2014 | Chon et al. |
| 2005/0010120 | A1 | 1/2005 | Jung et al. |
| 2005/0234361 | A1 | 10/2005 | Holland |
| 2005/0283090 | A1 | 12/2005 | Wells |
| 2007/0219453 | A1 | 9/2007 | Kremliovsky et al. |
| 2007/0219455 | A1 | 9/2007 | Wong et al. |
| 2007/0260151 | A1 | 11/2007 | Clifford |
| 2007/0265508 | A1 | 11/2007 | Sheikhzadeh-Nadjar |
| 2008/0065158 | A1 | 3/2008 | Ben-Ezra et al. |
| 2008/0097537 | A1 | 4/2008 | Duann et al. |
| 2008/0183093 | A1 | 7/2008 | Duann et al. |
| 2008/0200832 | A1 | 8/2008 | Stone |
| 2008/0228094 | A1 | 9/2008 | Audet et al. |
| 2008/0255464 | A1 | 10/2008 | Vincent |
| 2009/0069703 | A1 | 3/2009 | Takla et al. |
| 2009/0222262 | A1 | 9/2009 | Kim et al. |
| 2010/0056940 | A1 | 3/2010 | Moorman et al. |
| 2010/0234916 | A1 | 9/2010 | Turcott et al. |
| 2012/0165691 | A1 | 6/2012 | Ting et al. |
| 2012/0197144 | A1 | 8/2012 | Christ et al. |
| 2012/0232417 | A1 | 9/2012 | Zhang |
| 2013/0109937 | A1 | 5/2013 | Banet et al. |
| 2014/0005988 | A1 | 1/2014 | Brockway |

OTHER PUBLICATIONS

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d.

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long Qt in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

(56) References Cited

OTHER PUBLICATIONS

Inan, O.T.; Giovangrandi, L.; Kovacs, G.T.A.; Robust Neural-Network-Based Classification of Premature Ventricular Contractions Using Wavelet Transform and Timing Interval Features, IEEE Transactions on Biomedical Engineering vol. 53, Issue: 12, , pp. 2507-2515.
L. Smith, A tutorial on Principal Components Analysis.
Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.
K. Oweiss, A. Mason, Y. Suhail, A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering, vol. 54, No. 12, pp. 2172-2185 (2007).
X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).
R Schimpf, Ch Antzelevitch, D Haghi, C Giusetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008; 5(2): 241-245.
Sarkar S, Ritscher D, Mehra R. A detector for a chronic implantable atrial tachyarrhythmia monitor. IEEE Trans Biomed Eng. Mar. 2008;55(3):1219-24.
M. Malik, K. Hnatkova, T. Novotny, G Schmidt Subject-specific profiles of QT/RR hysteresis. Am J Physiol Heart Circ Physiol 295:H2356-H2363, 2008.
Akturk, A. and Goldsman, N. (2008) "Electron transport and full-band electron phonon interactions in graphene" J. of Applied Physics 103.
S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.
R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).
O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).
H. Li, R. Li, F. Wang. Multiresolution Subband Blind Source Separation: Models and Methods. Journal of Computers, vol. 4, No. 7 (2009), 681-688.
Afonso, V.X.; Tompkins, W.J.; Detecting ventricular fibrillation. IEEE Engineering in Medicine and Biology Magazine, vol. 14, Issue: 2, pp. 152-159.
Dash S, Chon KH, Lu S, Raeder EA. Automatic real time detection of atrial fibrillation. Ann Biomed Eng. Sep. 2009;37 (9):1701-9. Epub Jun. 17, 2009.
M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).
R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).
J. Piccini, et al, Predictors of sudden cardiac death change with time after myocardial infarction: results from the Valiant trial. European Heart Journal (2009).
J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).
S.Hadei, M. Iotfizad. A family of adaptive filter algorithms in noise cancellation for speech enhancement. International Journal of Computer and Electrical Engineering, vol. 2, No. 2, Apr. 2010. 1793-8163.
Allen, M., Tung, V., Kaner, R. (2010) "Honey Carbon: A Review of Graphene" Chem. Rev. 110:132-145.
Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.
HJ van der Linde, B Van Deuren, Y Somers, B Loenders, R Thwart and DJ Gallacher, The Electro-Mechanical window: a risk marker for Torsade de Pointes in a canine model of drug induced arrhythmias, British Journal of Pharmacology (2010) 161 1444-1454.
Daubechies I., et al. Synchrosqueezed wavelet transforms: an empirical mode decomposition-like tool. Applied and Computational Harmonic Analysis, vol. 30, Issue 2, Mar. 2011, pp. 243-261.
M. Brockway and R Hamlin, "Evaluation of an algorithm for highly automated measurements of QT interval," Journal of Pharmacological and Toxicological Methods, vol. 64, pp. 16-24 (2011).
http://www.physionet.org/physiobankidatabase/#ecg.
http://www.physionet.org/physiobankidatabase/mitdb/.
Tsalaile, et al. "Blind Source Extraction of Heart Sound Signals From Lung Sound Recordings Exploiting Periodicity of the Heart Sound," ICASSP 2008 IEEE, p. 461-464.
Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.
B. Widrow, et al., "Adaptive noise cancelling: principles and applications," IEEE Proc., vol. 63, No. 12, pp. 1692-1716, Dec. 1975.
H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).
G. Moody, W. Muldrow, and R. Mark, "A noise stress test for arrhythmia detectors," Computers in Cardiology, pp. 381-384 (1984).
K. R. Rao and P. Yip, "Discrete Cosine Transform: Algorithms, Advantages, Applications," San Diego, CA: Academic (1990).
J. Woods. Subband Coding, Kluwer Academic Press (1990).
K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).
NV Thakor and YS Zhu, "Applications of adaptive filtering to ECG analysis: noise cancellation," IEEE Transactions on Biomedical Engineering, vol. 38, No. 8, pp. 785-794 (Aug. 1991).
S. Mallat and W. L.-Hwang, "Singularity Detection and Processing with Wavelets," IEEE Transactions on Information Technology (38), pp. 617-643 (1992).
S. Mallat and S. Zhong, "Characterization of Signals from Multiscale Edges," IEEE Trans. Pattern Anal. Mach. Intell. 14, 7 (Jul. 1992).
Vaidyanathan, Multirate Systems and Filter Banks, Prentice Hall, 1993.
Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).
S. Mallat and Z. Zhang, "Matching Pursuits with Time-Frequency Dictionaries," IEEE TSP(41), No. 12, pp. 3397-3415 (Dec. 1993).
P. Comon, "Independent component analysis, a new concept?," Signal Process. Special Issue on Higher Order Statistics, vol. 36, No. 3, pp. 287-314 (Apr. 1994).
Donoho, D.L., I.M. Johnstone (1994), "Ideal spatial adaptation by wavelet shrinkage," Biometrika, vol. 81, pp. 425-455.

(56) References Cited

OTHER PUBLICATIONS

Y. Xu, J. Weaver, D. Healy, Jr. and J. Lu, Wavelet Transform Domain Filters: A Spatially Selective Noise Filtration Technique, IEEE Transactions on Image Processing, vol. 3, No. 6, pp. 747-758 (1994).
D. L. Donoho, "Denoising by Soft-Thresholding," IEEE Trans. on Inf. Theory, vol. 41, No. 3, pp. 613-627 (May 1995).
A.Bell and T. Sejnowski, "An Information-Maximization Approach to Blind Separation and Blind Deconvolution, "Neural Computation, 7:1129-1159. (1995).
M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).
V. Afonso, W. Tompkins, T. Nguyen, K. Michler and S. Luo, "Comparing Stress ECG Enhancement Algorithms," IEEE in Medicine and Biology, Engineering iology, pp. 37-44 (May/Jun. 1996).
J. Francois Cardoso, "Infomax and Maximum Likelihood for Source Separation," IEEE Letters on Signal Processing, vol. 4, No. 4, pp. 112-114 (Apr. 1997).
M. L. Hilton, "Wavelet and Wavelet Packets Compression of Electrocardiogram," IEEE Transactions on Biomedical Engineering, vol. 44, No. 5, pp. 394-402 (May 1997).
A. Hyvärinen, "New Approximations of Differential Entropy for Independent Component Analysis and Projection Pursuit," In Advances in Neural Information Processing Systems, vol. 10, pp. 273-279, MIT Press. (1997).
W. Sweldens. The lifting scheme: A construction of second generation wavelets. SIAM J. Math. Anal., 29(2):511-546, 1997.
American National Standard ANSI/AAMI EC57:1998, Testing and Reporting Performance Results of Cardiac Rhythm and ST Segment Measurement Algorithms.
Testing and reporting performance results of cardiac rhythm and ST-segment measurement algorithms ANSI/AAMI EC57:1998.
L. Torres- Pereira, et. al. "A Biotelemetric Heart Sound Monitoring System," in Proceedings of the 14th International Symposium on Biotelemetry. Marburg, 1998.
A. Hyvärinen, "Fast and Robust Fixed-Point Algorithms for Independent Component Analysis," IEEE Transactions on Neural Networks, vol. 10, No. 3, pp. 626-634 (May 1999).
J.-F. Cardoso, "High-Order Contrasts for Independent Component Analysis," Neural Comput., vol. 11, No. 1, pp. 157-192 (1999).
S. Chen, D Donoho, and M. Saunders, "Atomic Decomposition by Basis Pursuit," SIAM J. Scientific Computing, vol. 20, No. 1, pp. 33-61 (1999).
Q. Pan, L. Zhang, G. Dai and H. Zhang, "Two Denoising Methods by Wavelet Transform," IEEE Trans. on SP, vol. 47, No. 12, pp. 3401-3406 (Dec. 1999).
G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).
S. Mallat, "A Wavelet Tour of Signal Processing," Academic Press, 1999.
Langley, P.; Di Bernardo, D.; Murray, A.; Comparison of three measures of QT dispersion. Computers in Cardiology 1999 pp. 69-72.
Goldberger AL et al. PhysioBank, PhysioToolkit, and PhysioNet: components of a new research resource for complex physiologic signals. Circulation 101(23): e215-e220, 2000 (Jun. 13).
Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).
M. Marcellin, M. gormish, A. Bilgin and M. Boleik, "An Overview of JPEG-2000," Proc. of IEEE Data Compression Conference, pp. 523-541 (2000).
L. K. Saul and J. B. Allen, "Periodic component analysis: An eigenvalue method for representing periodic structure in speech," in NIPS, [Online]pp. 807-813 (2000). Available: http://www.cs.cmu.edu/Groups/NIPS/00papers-pub-on-web/SaulAllen.pdf.
C. Taswell, "The What, How, and Why of Wavelet Shrinkage Denoising," Computing in Science and Engineering, vol. 2, No. 3, pp. 12-19 (2000).
J. S. Richman and J. R. Moorman, Physiological time-series analysis using approximate entropy and sample entropy Am. J. Physiol. 278, H2039 (2000).
K. Sayood, "Introduction to Data Compression," Academic Press 2000.
Malik M, Batchvarov VN. Measurement, interpretation and clinical potential of QT dispersion. J Am Coll Cardiol. Nov. 15, 2000;36(6):1749-66.
A. Hyvärinen and E. Oja, "Independent Component Analysis: Algorithms and Applications," Neural Networks, 13(4-5), pp. 411-430 (2000).
R. Mayerburg. Sudden cardiac death: exploring the limits of our knowledge. Journal of Cardiovascular Electrophysiology, vol. 12, No. 3, Mar. 2001.
M. Brennan, M. Palaniswami, and P. Kamen. Do Existing Measures of Poincare Plot Geometry Reflect Nonlinear Features of Heart Rate Variability? IEEE Transactions on Biomedical Engineering, vol. 48, No. 11, Nov. 2001.
D. Donoho and X. Huo, "Uncertainty Principles and Ideal Atomic Decomposition," IEEE Transactions on Information Theory, vol. 47, No. 7, pp. 2845-2862 (Nov. 2001).
M. Zibulevsky and B. Pearlmutter, "Blind Source Separation by Sparse Decomposition in a Signal Dictionary," Neural Computation. vol. 13, pp. 863-882 (2001).
Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.
M. Costa, A. L. Goldberger, and C.-K. Peng, Multiscale Entropy Analysis of Complex Physiologic Time Series, Phys. Rev. Lett. 89, 6, (2002).
B. U. Kohler, C. Hennig, R. Orglmeister. The principles of software QRS detection. IEEE Engineering in Medicine and Biology Magazine, vol. 21, No. 1, (2002), pp. 42-57.
Kellermann, et al.,"A mobile phone based alarm system for supervising vital parameters in free moving rats," BMC Research Notes 2012, 5:119, Feb. 23, 2012.
http://www.simplehelp. net/2006/09/12/how-to-set-up-outlook-2003-for-email/.
Lee, J., "Time-Varying Coherence Function for Atrial Fibrillation Detection". IEEE Transactions on Miomedical Engineering vol. 60, No. 10, Oct. 2013.

METHOD AND APPARATUS FOR DETECTION OF HEARTBEAT CHARACTERISTICS

FIELD OF INVENTION

Various aspects of the present invention relate to the processing of physiological signals, such as electrocardiogram (ECG) and other signals indicative of the activity of a beating heart, and more particular aspects relate to detection of the presence of heartbeat characteristics.

BACKGROUND

Analysis of the character of the variability of heart beats can provide valuable insights that can be useful for diagnosis and monitoring of pathological conditions such as atrial fibrillation (AF) or the presence of other heartbeat characteristics such as ectopic beats. AF is a cardiac disorder that occurs when the heart's upper chambers (the atria) quiver instead of beating effectively. With AF, blood may not be pumped completely out of the atria, allowing blood to pool in the atria and eventually form a clot. If a clot migrates from the left atria it may travel through the arterial system and lodge in the brain, resulting in stroke. A high proportion of AF is asymptomatic and therefore one cannot rely on the patient to report its presence or absence. Assessing the presence of AF is therefore important to establish a diagnosis, choose appropriate therapy and monitor the patient following administration of a therapeutic regimen to determine its effectiveness.

In a normal heart, electrical activity of the atria is quite regular. When the atria contracts, an ECG recorded from electrodes located on the chest will typically show a small deflection corresponding to electrical activity in the atria (i.e. P-wave). When atrial electrical activity reaches the "atrioventricular" (AV) node, it is delayed to allow the atria to finish contracting and expelling blood into the ventricles. Following the delay in the AV node, the electrical activity travels into the ventricles, causing them to contract and pump blood throughout the body.

When AF is present, the AV node is bombarded with a highly variable level of electrical activity from the atria at a rate much faster than its conduction delay can accommodate. As a result, much of the electrical atrial activity from the atria is blocked. Due to this and the stochastic nature of the atrial electrical activity, the AV node stimulates the ventricles in an irregular pattern. AF can therefore usually be detected by evaluating ventricular activity. When physicians examine ECG recordings for the presence of AF, they often describe what they are looking for in the ventricular rhythm as the degree of irregularity in the irregularity. If the irregularity is regular, such as in bigeminy or trigeminy, AF is not present. Likewise if the patient has a strong sinus arrhythmia, as is often the case when a patient is in good physical condition, the rhythm is irregular but is regularly irregular. The irregularity has a regular pattern that correlates with respiration. When AF occurs, the irregularity is highly stochastic.

AF is often transient and therefore requires that the patient be monitored for days or weeks in order to obtain an accurate assessment of the presence of AF and the degree to which it is present (i.e. AF burden). This long-term monitoring often is performed with a small battery-powered wearable device that continuously evaluates the ECG and detects the occurrence of AF and other cardiac arrhythmias. Since the device is battery powered, computational efficiency of the detection algorithm is important.

While approaches to AF detection have been implemented, their implementation has been challenging. For example, detection of AF based upon the irregularity of ventricular rhythm can result in false positive detections when, for example, the patient is experiencing bigeminy, trigeminy or strong sinus arrhythmia. In addition, many approaches are computationally burdensome, which can require large power consumption (e.g., resulting in the need for a large battery and hence large device size and weight), and suffer from short battery life.

SUMMARY

Various aspects of the present invention are directed to devices, computer implemented methods and systems for detecting the presence of AF, in a manner that addresses challenges and limitations including those discussed above. Certain embodiments provide an indication of AF based on the presence of ectopic beats, which can mitigate the detection of false positive AF event detections. Accurate AF detection can be provided by considering whether P-waves are present. In connection with various embodiments, it has been discovered that approaches as characterized herein can mitigate computational burden and lower power consumption.

In accordance with various example embodiments, QRS complexes are detected in an ECG and a sequence of inter-beat intervals is computed. The sequence of inter-beat intervals is cleaned by identifying QRS complexes to be excluded, reducing or eliminating inter-beat intervals that relied on excluded QRS complexes, and interpolating across the gaps created by the excluded QRS complexes.

In one aspect, QRS complexes to be excluded are those that are detected in error, were excessively noisy and hence of suspect accuracy, or were part of a ventricular arrhythmia. The cleaned inter-beat interval sequence is decomposed into subcomponents. As may be implemented with one or more embodiments, the interbeat interval sequence is resampled to create equispaced series prior to decomposition. In another embodiment the decomposition is performed on interbeat interval sequence that is not resampled. In one example embodiment, an envelope V(t) is computed using one or more selected subcomponents. In one embodiment, one subcomponent is selected and V(t) is computed as the absolute value or the square root of the square of the selected subcomponent. In one embodiment, the selected subcomponent is the subcomponent that corresponds to the highest frequency represented by the decomposition. In another embodiment, the envelope V(t) is computed using a subcomponent with a corresponding frequency in the range of 0.5 to 3 Hz for adult human beings and 0.2 to 1 times the highest heart rate for other species. In another embodiment, an envelope V(t) is computed by computing the square root of the sum of the squares of two or more selected subcomponents at each time point. In one embodiment the envelope V(t) is computed by applying a low pass filter to the point-wise square of the selected subcomponents prior to computing the square root.

In an alternate embodiment a time-frequency spectrum is computed using, for example, continuous wavelet decomposition or short-term Fourier transform. The resulting spectrum is divided into frequency bands, and envelope V(t) is computed. V(t) in this embodiment represents the power in one or more frequency bands as a function of time.

According to one aspect of the present invention, V(t) is compared to a threshold Vth. When V(t) exceeds the threshold Vth for more than a predetermined time T1 (e.g., a time exhibiting power greater than Vth in one or more frequency bands), a metric of the entropy SE(t) of one or more subcomponents SUB(t) or their point-wise products is computed from the time when V(t) first crossed threshold Vth. If SE(t) is greater than a threshold SEth (an entropy threshold), the presence of AF is indicated. Such a threshold may, for example, pertain to a signal having an irregularly irregular sequence of interbeat intervals.

Once the presence of AF is established, V(t) is evaluated to determine if the AF event has terminated. In one embodiment, V(t) is evaluated relative to a threshold Vthl to determine if the AF event has terminated. If V(t) falls below threshold Vthl for a time>T2, then the absence of AF is indicated. T1 and T2 are selected based upon clinically significant intervals for which it is important to detect the presence or absence of AF. In one embodiment T1 and T2 are at least 30 sec.

The above summary is not intended to describe each embodiment or every implementation of the present disclosure. The figures and detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1:
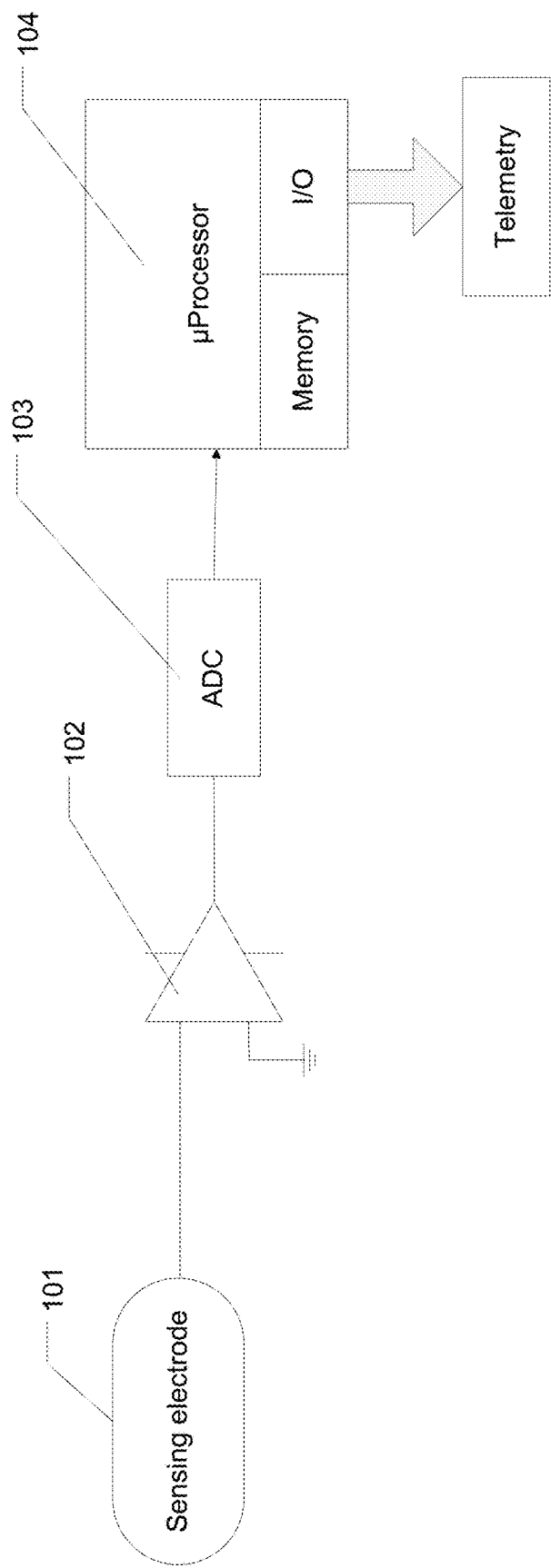
FIG. 1 illustrates an apparatus for sensing, measuring and processing an ECG signal for detecting the presence of AF.

While the invention is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

Various example embodiments of the present disclosure relate to methods, circuits, computer implemented software, devices and systems that use physiological signals for detecting the presence or absence of AF. While the present disclosure is not necessarily limited in this regard, various aspects of the disclosure may be appreciated through a discussion of examples using this context.

As discussed hereinabove, various circuits, devices and systems that process physiological signals (e.g., ambulatory ECG recordings) can be challenging to implement for accurately detecting the presence and absence of AF, and may not be efficient in use of power. Accurate detection of AF presents a significant challenge to the implementation of such circuits, computer implemented software, devices and systems for carrying out signal evaluation. Accordingly, various aspects of the present invention are directed to addressing these challenges.

In accordance with another example embodiment, a computer implemented method involves detecting the presence of AF in a recording of activity of a beating heart. A time series of inter-beat intervals is computed from the recording, and the time series is decomposed into subcomponents. An envelope of at least one of the subcomponents is computed, and the presence of AF is detected based upon characteristics of the envelope that are indicative of AF (e.g., based upon a comparison of the envelope to a first threshold indicative of AF).

In some embodiments, computing a time series of inter-beat intervals includes detecting a plethora of heart beats, identifying invalid beats from the detected beats, and computing a raw sequence of inter-beat intervals from consecutive ones of the detected beats. A cleaned sequence of inter-beat intervals is created/identified by excluding intervals computed using ones of the beats identified as being invalid. The cleaned sequence of inter-beat intervals is then resampled to create an equispaced time series of inter-beat intervals. In some implementations, invalid beats are identified as beats characterized as one or more of ventricular arrhythmias, being detected in error, and excessively noisy (e.g., beyond a noise threshold determined for particular applications/desirable output).

Detecting the presence of AF can be carried out in a variety of manners. In some embodiments, detecting the presence of AF includes detecting the presence of AF based upon an envelope exceeding a first threshold for predetermined amount of time, as discussed above. In another embodiment, AF is detected based upon such an envelope exceeding the first threshold for a predetermined portion of a predetermined amount of time, and a computed metric of entropy exceeding an entropy threshold. Certain embodiments involve computing the metric of entropy, such as for one or more of the time series of inter-beat intervals, a subcomponent, and a product of subcomponents. In some embodiments, the metric of entropy is computed using one of sample entropy and approximate entropy. In another embodiment, AF is detected based upon an envelope falling below a second threshold for a predetermined portion of a predetermined time.

A variety of recordings may be processed in accordance with embodiments described herein. Such recordings may include, for example, an electrocardiogram, a ballistocardiogram, heart sounds, blood pressure, blood flow in an artery, and a photoplethysmography signal of a body tissue. In addition, decomposing the time series into subcomponents is carried out in a variety of manners to suit particular embodiments, such as by applying one of a discrete cosine transform, a stationary wavelet transform, a discrete wavelet transform, a filter bank, a synchrosqueezed wavelet transform, a Gabor transform, a short-term Fourier transform, a continuous wavelet transform and a wavelet packet transform. In some embodiments, one or more of the subcomponents are identified as a subcomponent having a frequency corresponding to a highest frequency of the subcomponents.

In one embodiment the presence of AF is detected. Referring to FIG. 1, an ECG signal is captured via sensing electrode (or electrodes) 101, is amplified with amplifier 102, digitized with ADC 103, and the digitized signal is processed using a computerized algorithm implemented in computing device 104. It should be recognized that signals other than ECG can be captured by sensing electrode 101 for detection of AF. These signals include arterial blood pressure, a photoplethysmography signal obtained from the tissue, an acoustical signal sensed from the thorax, and a ballistocardiogram.

Figure 2:
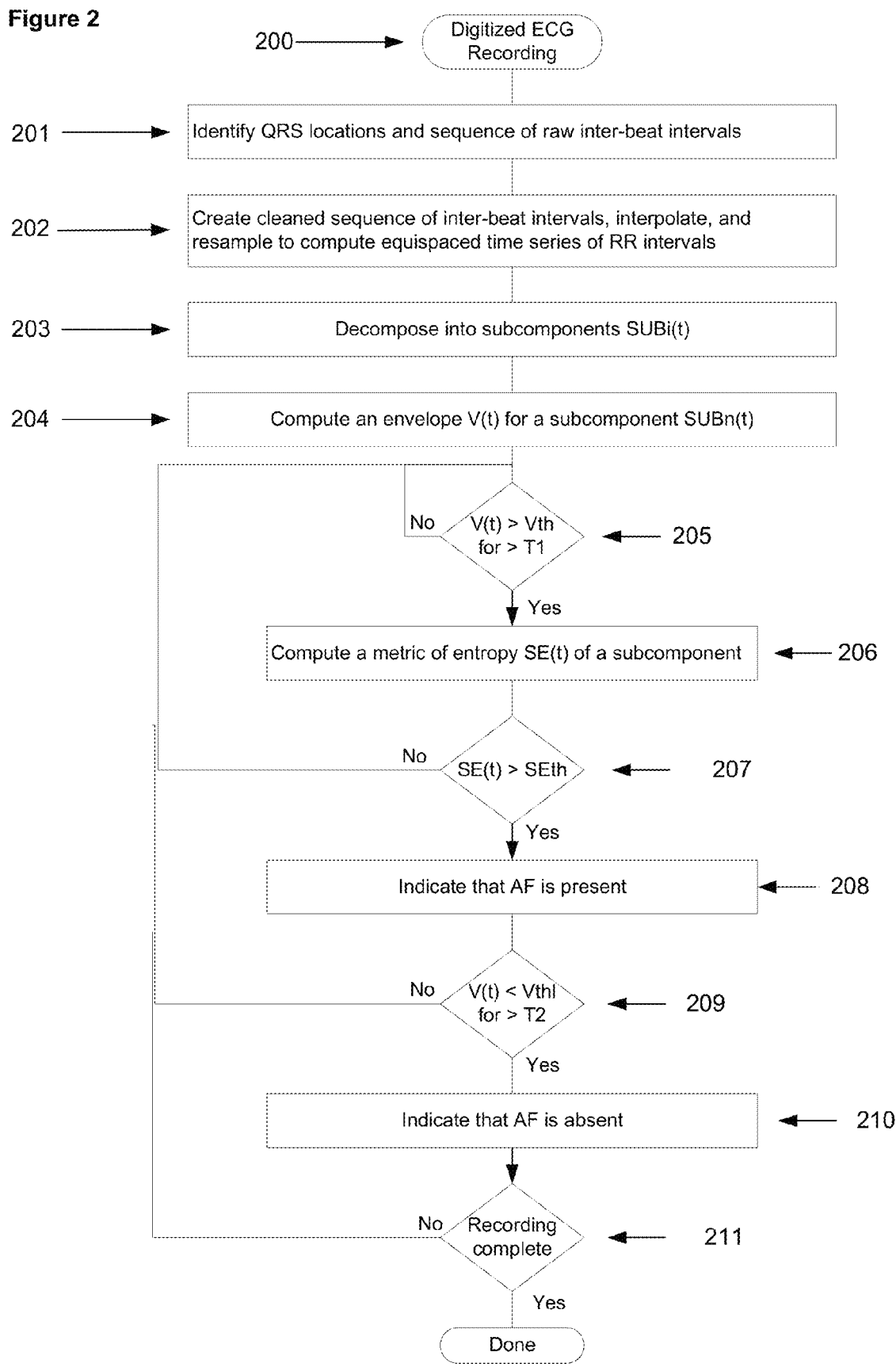
FIG. 2 shows a flowchart describing signal flow for detecting the presence and absence of AF.

Referring to FIG. 2, a digitized ECG recording 200 is input in 201 and is processed using a computerized algorithm to identify the locations of QRS complexes and a sequence of raw inter-beat intervals is computed as the time between adjacent QRS complexes. In one embodiment, QRS complexes are identified using an approach as described in U.S. Pat. No. 8,632,465 and PCT publication PCT/US2013/024770. In another embodiment, QRS complexes are identified using a Pan-Tomkins approach as described in Pan J., Tompkins W. A Real-Time QRS Detection Algorithm. IEEE Transactions on Biomedical Engineering, vol. BME-32, no. 3, March 1985, which is fully incorporated herein by reference. In another embodiment, QRS complexes are identified using a Hilbert transform as described in U.S. Pat. No. 7,729,753.

In some embodiments, as shown in step 202, it is useful to create a cleaned and equispaced sequence of inter-beat intervals. Cleaning can be accomplished by identifying QRS complexes that were falsely triggered by noise in the ECG recording or are associated with ventricular arrhythmias, ignoring associated inter-beat intervals, and interpolating over the gaps created by ignoring these intervals. Ventricular arrhythmias can be identified using techniques as described herein and/or well known in the art. Ventricular arrhythmias to be excluded may include ectopic beats, ventricular tachycardia, pause and bradycardia. In some embodiments, detection of QRS complexes that are falsely triggered by noise is accomplished by measuring noise level in the ECG signal and computing a confidence in the QRS detection based upon the level of noise. One technique for computing this confidence signal is described in U.S. Pat. Nos. 8,632,465 and 8,433,395. Certain embodiments employ other techniques for noise measurement such as measurement of zero crossings in the isoelectric line between T-wave offset and P-wave onset can also be used, for example, U.S. Pat. No. 7,515,955. In some embodiments, the cleaned sequence of RR intervals is fit with a cubic spline function and then resampled to create a cleaned and equispaced time series of RR intervals. In another embodiment, the cleaned sequence of RR intervals is linearly interpolated to create an equispaced series of RR intervals.

The time series resulting from step 202 is then decomposed into subcomponents SUBi(t) in 203 using one of several transforms. In some embodiments the decomposition can be accomplished using one of a discrete cosine transform, a stationary wavelet transform, a discrete wavelet transform, a filter bank, a synchrosqueezed wavelet transform, a Gabor transform, a short-term Fourier transform, continuous wavelet transform, or wavelet packet transform.

An envelope V(t) of a subcomponent SUBn(t) is computed in 204. In one embodiment, envelope V(t) is computed using the subcomponent corresponding to the highest frequency, SUBn(t). In some embodiments, the envelope is computed as the absolute value of SUBn(t), ABS(SUBn(t)). In other embodiments, ABS(SUBn(t)) is smoothed by applying a low-pass filter. In other embodiments V(t) is computed as the square root of the square of the subcomponent SUBn(t). In yet another embodiment, envelope V(t) is computed using multiple subcomponents, each corresponding to a different frequency. In one embodiment, multiple subcomponents are combined using various weighting factors applied to the absolute values of each subcomponent used to compute V(t).

In another embodiment, the envelope V(t) is computed using a subcomponent with a corresponding frequency in the range of 0.5 to 3 Hz for adult human beings and 0.2 to 1 times the frequency corresponding to the highest heart rate for other species. If V(t) exceeds a predetermined threshold for a time>T1, there is a preliminary indication that AF may be present. Time interval T1 can be determined by the shortest duration AF event that is desired to be detected. For example, if it is desired to detect AF events of 30 seconds and longer, T1 may be 30 seconds. In another embodiment, an envelope is computed as the square root of the sum of the squares of two or more selected subcomponents at each time point. In one embodiment the envelope V(t) is computed by applying a low pass filter to the point-wise square of the selected subcomponents prior to computing the square root.

In another embodiment a time-frequency spectrum is computed using, for example, a continuous wavelet decomposition or short-term Fourier transform. The resulting spectrum is divided into frequency bands, and an envelope V(t) is computed on the selected frequency bands. The envelope V(t) in this embodiment, represents the power in a band of frequencies as a function of time.

Envelope V(t) is compared to a threshold Vth in 205. If V(t) exceeds Vth for a predetermined time interval T1, a metric of signal regularity or complexity is computed. In another embodiment, V(t) must exceed Vth for more than a predefined portion of T1. In one embodiment, V(t) must exceed Vth for at least 90% of T1. In another embodiment, V(t) must exceed Vth for at least 60% of T1. In one embodiment, entropy SE(t) is computed as a metric of complexity. In some embodiments, SE(t) is computed using sample entropy as in Richman J S, Randall M J, "Physiological time-series analysis using approximate entropy and sample entropy," Am J Physiol Heart Circ Physiol 278:H2039-H2049 (2000), which is fully incorporated herein by reference. In another embodiment SE(t) is computed using approximate entropy, such as in Pincus S M, "Approximate entropy as a measure of system complexity," Proc Natl Acad Sci USA 88:2297-2301 (1991), which is fully incorporated herein by reference. In other embodiments one or more of detrended fluctuation analysis (DFA), correlation dimension, largest Lyapunov exponent, fractal dimension, Hurst exponent, and recurrence plots are used as metrics of regularity or complexity. DFA quantifies the extent of short and long-range correlations in a time series, via a metric called a scaling exponent. In one embodiment, the fluctuations of a detrended integrated time RR time series are calculated as root mean square values F(n) of individual subcomponents SUBn(t)s. The scaling exponent is then approximated as a slope a of the linear fit in the log-log plot: log F(n)=α log n. When scaling exponent a at around 0.5, the time series dynamic is similar to white noise, which is characteristic of RR time series in AF.

In one embodiment, the energy of higher frequency beat-to-beat fluctuations in RR interval is computed. In some embodiments premature beats are identified (premature beats of either ventricular or atrial origin) and excluded prior to computing the energy of higher frequency beat-to-beat fluctuations. This computed measure of energy is indicative of the higher frequency changes in RR interval that correspond to those typical of AF. Lower frequency changes in RR interval that are not indicative of the presence of AF (e.g., those corresponding to respiratory sinus arrhythmia and changes in physical activity) are not included in this energy measure. An envelope of the higher frequency energy is computed. When the envelope exceeds a threshold for a predetermined time, the series of RR intervals is determined to be sufficiently irregular to indicate that AF might be present. Once it is established that AF may be present, a metric of entropy (i.e., chaos) is computed for the series of RR intervals to confirm the presence of AF. In some embodiments it is advantageous to compute entropy only after a first order irregularity is found because entropy algorithms are generally computationally demanding.

In one embodiment approximate entropy is computed as a measure of the degree of chaos in the inter-beat time series. Approximate entropy (APE) quantifies the probability that a 'similar' pattern will not be followed by additional 'similar' patterns throughout the series. The algorithm for computing APE depends upon two parameters: length of the chosen pattern (m) and threshold for similarity between patterns (r). The algorithm for computing APE involves computing conditional probability that any two sequences of length m that match within tolerance of r will also match at the m+1 point.

In another embodiment sample entropy is computed as a measure of the degree of chaos in the inter-beat time series. Similar to approximate entropy the algorithm involves computing conditional probability of pattern matching. In some embodiments, relative to sample entropy, approximate entropy compensates for bias introduced by matching a template to itself and the sensitivity of the conditional probability to the time series length.

Entropy SE(t) is computed in 206 for a subcomponent SUBn(t) starting when V(t) first exceeds threshold Vth. In an alternate embodiment, SE(t) is computed from the RR time series. In yet another embodiment, SE(t) is computed from a product or a linear combination of the subcomponents. In one embodiment, SE(t) is computed for consecutive one-minute segments. In other embodiments, entropy is computed for overlapping segments or segments that are shorter or longer.

In yet another embodiment where V(t) is computed using subcomponents corresponding to a band of frequencies in a time-frequency spectrum, SE(t) is computed using one or more subcomponents corresponding to a band of frequencies. In another embodiment SE(t) is computed using a product or a linear combination of the subcomponents corresponding to the selected band of frequencies. If SE(t) exceeds a predetermined threshold SEth in 207, the presence of AF is detected in 208.

Figure 5:
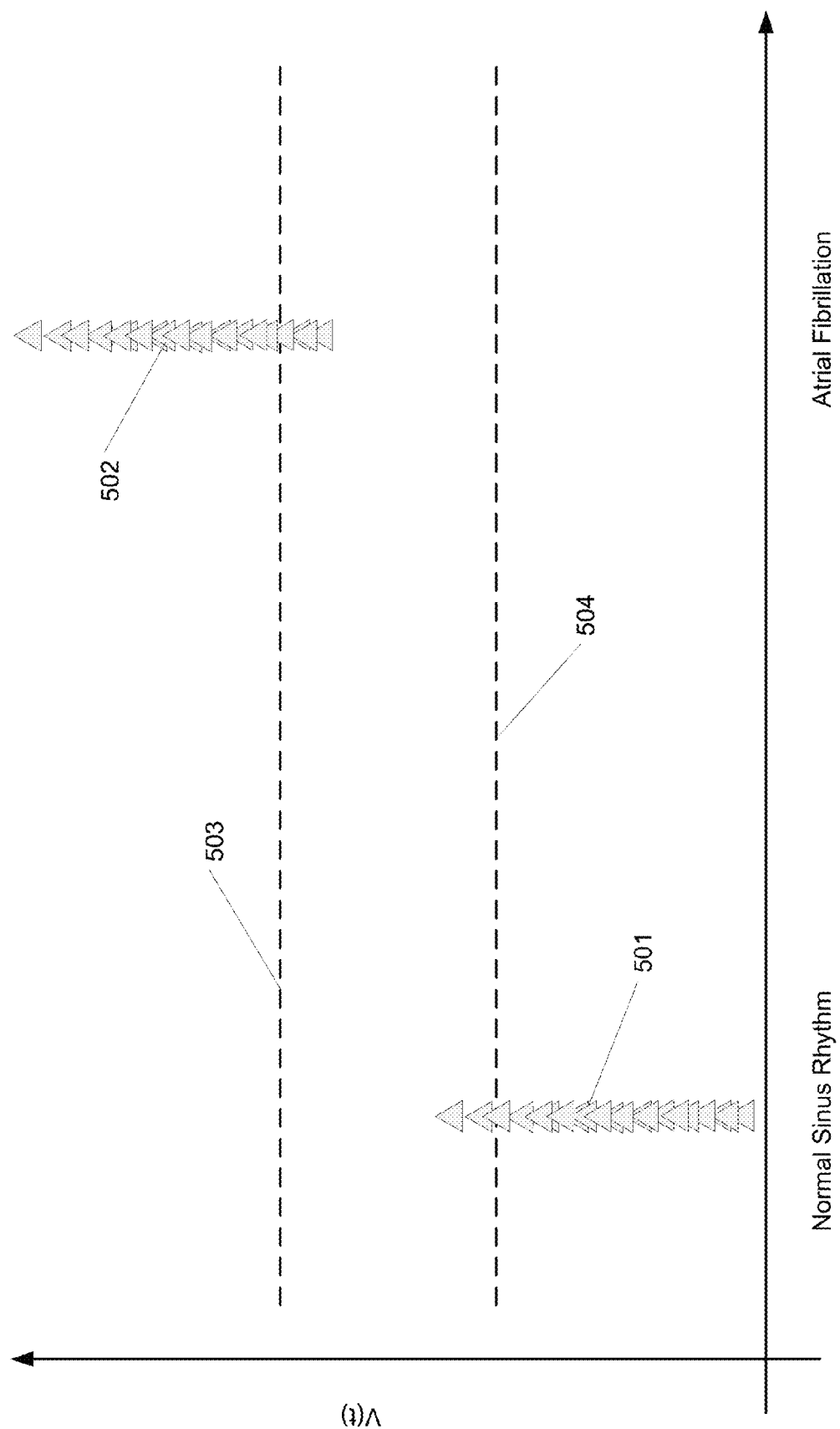
FIG. 5 shows an example embodiment for determining Vth and Vthl.

In one embodiment, the threshold Vth is determined empirically based upon the characteristics of RR dynamics of the species. The second threshold Vthl evaluated in step 209, (i.e. the lower threshold that together with Vth provides hysteresis, or Schmitt trigger, operation for detection of the presence and absence of AF) can be likewise determined empirically. In one embodiment, Vth and Vthl are determined by computing envelope V(t) for a representative ECG data set consisting of normal sinus rhythm and AF events. In one embodiment, amplitude of V(t) is plotted vs. rhythm classification (i.e. normal sinus rhythm and AF), resulting in two clusters as shown in FIG. 5. Thresholds Vth and Vthl are selected as values that separate the amplitudes of V(t) for these two classifications to a desired statistical confidence level. In one embodiment, Vth is chosen as the $10^{th}$ percentile of the envelope amplitude for the AF cluster and Vthl is chosen as the $95^{th}$ percentile of the envelope amplitude for the normal sinus rhythm cluster. Percentiles used for determining Vth and Vthl can vary depending upon the desired tradeoff between sensitivity and specificity of AF detection performance.

FIG. 5 shows an example embodiment for how Vth and Vthl are determined. Cluster 501 consists of values of V(t) for normal sinus rhythm. Cluster 502 includes values of V(t) for when AF is present. In this example embodiment, threshold Vth 503 is chosen as the $10^{th}$ percentile of values of V(t) for AF events and Vthl 504 is chosen as the $95^{th}$ percentile of V(t) for ECG recordings classified as normal sinus rhythm.

In one embodiment, a metric of entropy SE(t) is used to discriminate between AF and rhythms that demonstrate a high degree of irregularity in RR interval, but are regular in the nature of the irregularity (i.e. bigeminy, trigeminy and respiratory sinus arrhythmia). SE(t) is compared to a threshold SEth in 207 to discriminate between AF and rhythms that are characteristically regular in the nature of their irregularity.

In some embodiments, threshold SEth in 207 in FIG. 2 is determined empirically in a manner similar to how Vth and Vthl are determined. In one embodiment, SE(t) is plotted vs. rhythm classification resulting in two clusters: one for AF and a second corresponding to bigeminy, trigeminy and high amplitude respiratory sinus arrhythmia. In one embodiment SEth is chosen as the $95^{th}$ percentile of the cluster comprised of rhythms having a characteristic of regular irregularity such as bigeminy, trigeminy and respiratory sinus arrhythmia. The percentile used for determining SEth can vary depending upon the desired tradeoff between sensitivity and specificity of AF detection performance. In some embodiments, it may be useful to implement a second threshold such that hysteresis (i.e. Schmitt trigger functionality similar to an embodiment of how V(t) evaluation vs. Vth and Vthl) can be implemented to improve discrimination of AF from bigeminy, trigeminy and high amplitude respiratory sinus arrhythmia.

Figure 6:
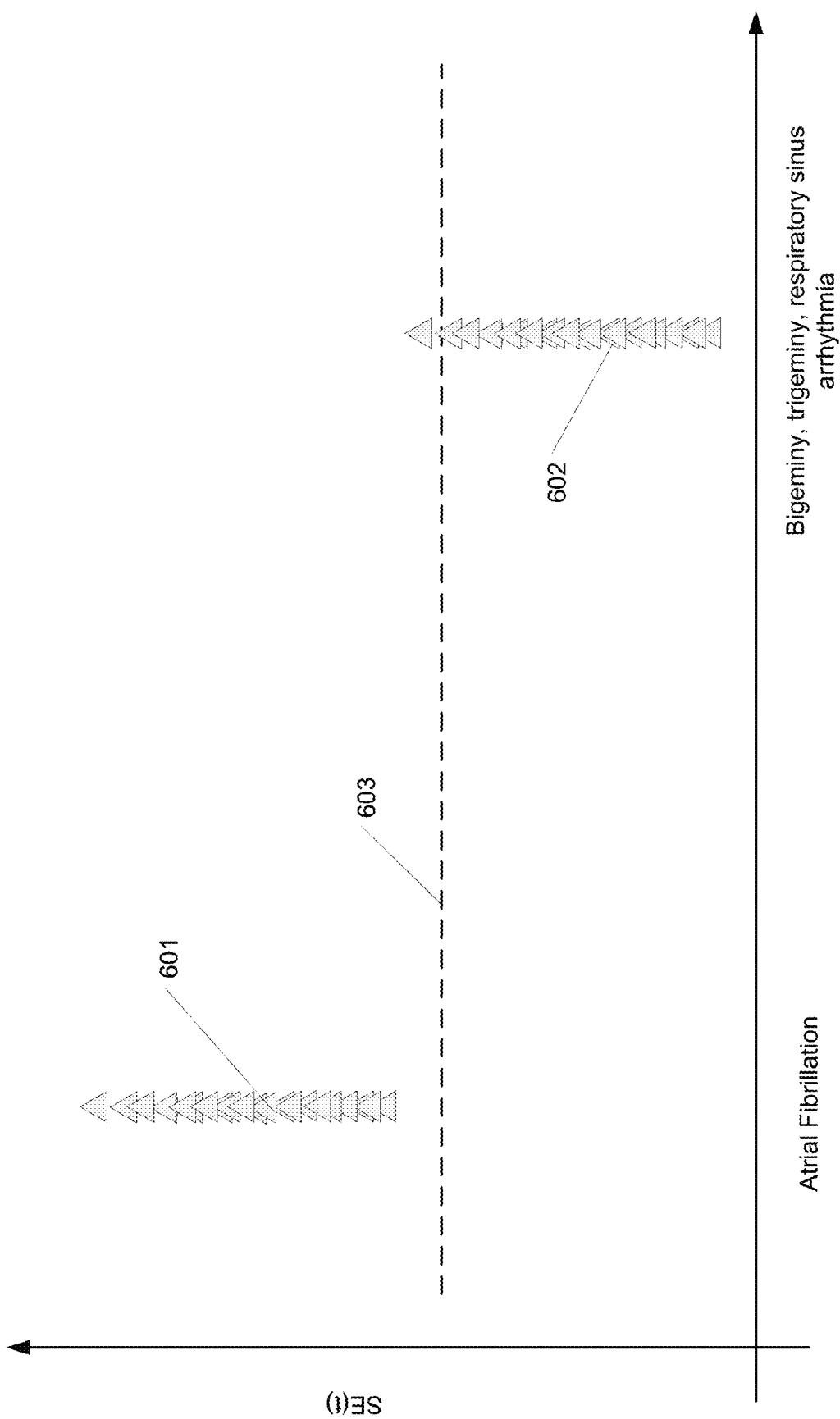
FIG. 6 shows an example embodiment for determining signal entropy threshold SEth.

FIG. 6 shows an example embodiment demonstrating how SEth is determined. Cluster 601 consists of values of SE(t) for ECG strips where AF is present. Cluster 602 consists of values of SE(t) for when bigeminy, trigeminy or high amplitude respiratory sinus arrhythmia is present. In this example embodiment, threshold SEth 603 is chosen as about the $95^{th}$ percentile of SE(t) for ECG recordings classified as bigeminy, trigeminy or high amplitude respiratory sinus arrhythmia.

Once the presence of AF has been detected, and referring again to FIG. 2, envelope V(t) is evaluated to determine if AF is absent by comparing V(t) to a threshold Vthl in 209, where Vthl<Vth. In one embodiment, the algorithm will continue to indicate that AF is present until V(t) falls below Vthl for a predetermined time T2. In yet another embodiment, AF is detected as being absent when V(t) falls below Vthl for at least 60% of time T2. Once it is determined that AF is absent at 210, the algorithm will then begin to look for the onset of AF by evaluating V(t) in 205. The process ends if the recording is complete at block 211, and continues at block 205 if not.

Figure 3:
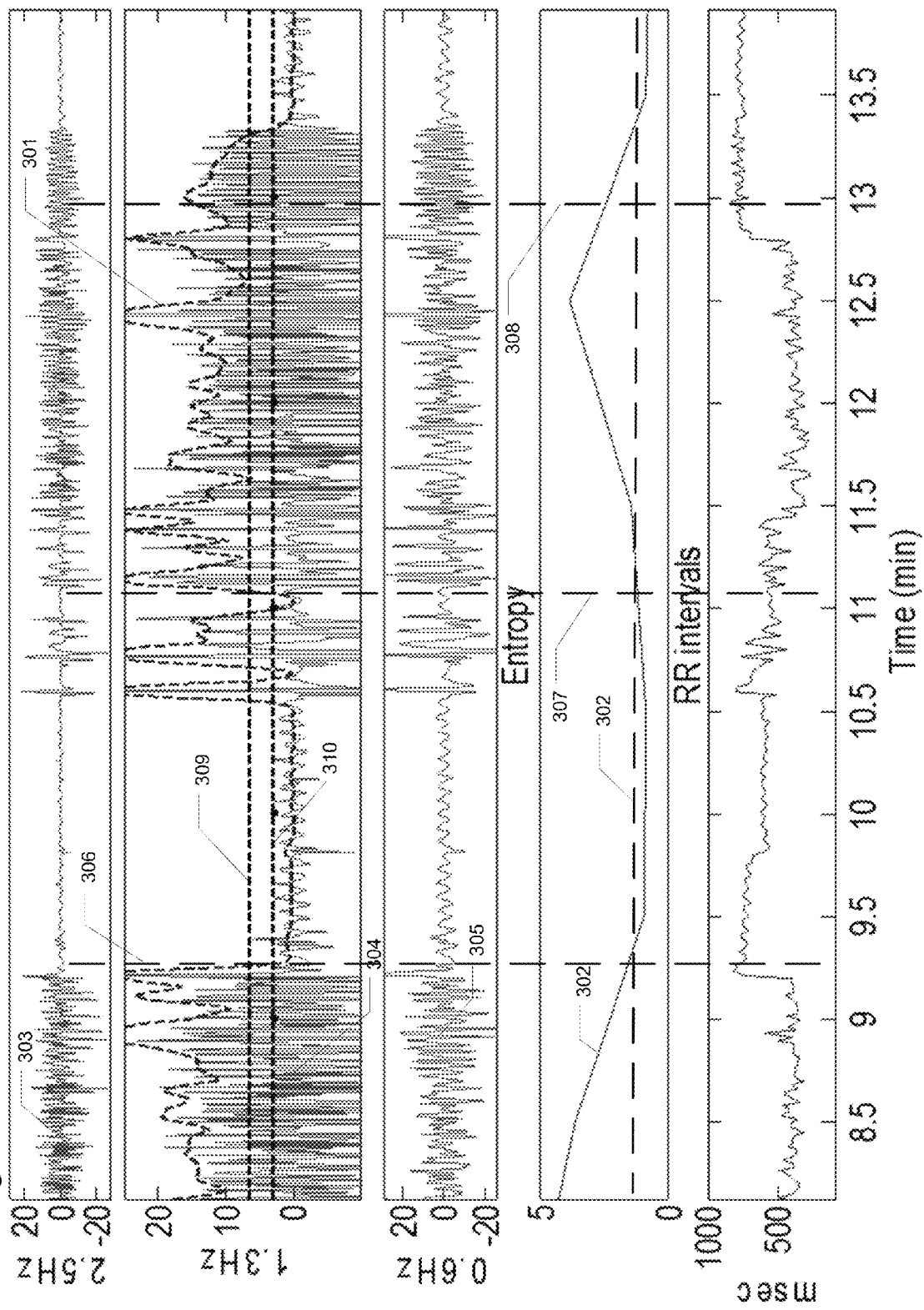
FIG. 3 shows a plot of various signals computed before, during, and after the detection of the presence of AF.

An example recording is shown in FIG. 3 for illustrative purposes. Traces 303, 304 and 305 are the subcomponents corresponding to the highest three frequencies following decomposition. Envelope 301 is computed using subcomponent 304, the second highest frequency subcomponent and corresponds to V(t) computed in 204 of FIG. 2. Threshold 309 corresponds to Vth in 205 of FIG. 2 and SE(t) 302 shows the entropy metric over time as computed in 206 of FIG. 2. In this example, entropy is computed on one minute segments of subcomponent 304. The value of entropy metric SE(t) at about 13.5 minutes, for example, is computed based upon subcomponent 304 in the prior one minute segment.

FIG. 3 begins at about 8 minutes into the recording with the presence of AF having already been detected. Envelope V(t) 301 remains above threshold Vthl 310 until about time 9.2 minutes. V(t) 301 falls below Vthl 310 and remains below threshold 310 for the requisite time T2 as examined in 209 of FIG. 2. The absence of AF is indicated at vertical dashed marker 306 at the time point where V(t) 301 falls below Vthl 310.

The recording then progresses in time with V(t) 301 below Vth 309 until about time 11.1 minutes. V(t) 301 then crosses threshold Vth 309 and remains above for the requisite time. SE(t) 302 at 11.5 minutes, the value computed for the prior one minute segment, is above threshold SEth 302 and therefore the presence of AF is indicated where V(t) 301 first crossed threshold Vth 309 indicated by marker 307. V(t) 301 remains above threshold Vthl 310 until about time 13.3 minutes. However, an episode of bigeminy starts at about 12.8 minutes, causing entropy metric 302 computed at time 13.5 minutes to fall below threshold SEth. The absence of AF is therefore indicated 30 seconds prior to where entropy metric 302 was computed (one-half the 60 second segment length used for computing entropy) per marker 308. Note that V(t) remains well above Vthl until about time 13.3 minutes.

Figure 4:
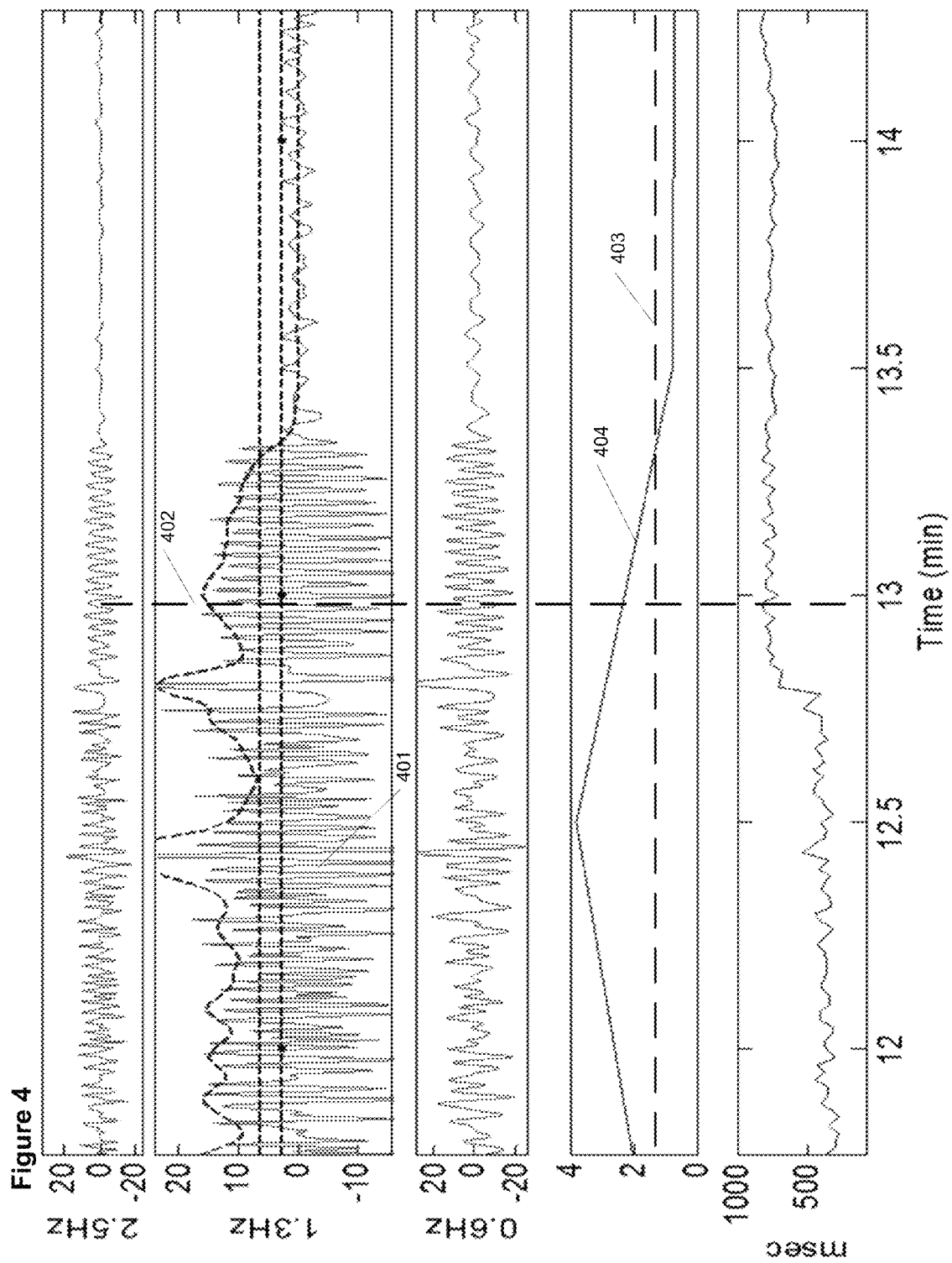
FIG. 4 shows a plot of various signals computed during and after detection of the presence of AF.

FIG. 4 provides an enlarged view of FIG. 3 from about 11.8 to 14.2 minutes for illustrative purposes. Note that subcomponent 401 transitions from chaotic to regular at about 12.8 minutes, the point where the ECG transitions from AF to bigeminy. Entropy metric 404 computed at time 13.5 minutes includes a portion of subcomponent 404 which was chaotic for about the first 20 seconds and regular for the last 40 seconds. Entropy metric 404 was evaluated vs. SEth (as in step 207 of FIG. 2) at time 13.5 minutes and was found to be below threshold SEth 403. The absence of AF was therefore indicated 30 seconds prior at marker 402.

A challenge to the accurate determination of the presence of AF is the ability to detect a type of ventricular arrhythmia referred to as ectopic beats and exclude the corresponding inter-beat intervals. In some patients ectopic beats occur frequently and in an irregular pattern. In order to avoid false positive detections of AF, it is necessary to detect most of these ectopic beats and exclude them in step 202 of FIG. 2 while creating a cleaned sequence of inter-beat intervals. In some embodiments, the incidence of ectopic beats is detected and/or reported, such as to provide diagnostic information for patient management or to assess the effect of a drug or other therapy.

In some embodiments, detection of ectopic beats can be achieved by decomposing the input ECG signal into subcomponents and computing the ratio of the energy of one or more low-frequency subcomponents to the energy of one or more high-frequency subcomponents. In one embodiment, a window is formed around a detected ventricular depolarization (e.g., as detected when a ventricle contracts, as may relate to the QRS complex or ectopic beats). The depolarization may consist of a sinus complex or an ectopic ventricular beat. Energy contained in two or more scales within the window is computed and compared to assess whether the beat contained in the window is a sinus complex or an ectopic beat. In one embodiment the two or more scales consist of a low-frequency scale and a high frequency scale. In some embodiments energy of a scale is computed as the sum of squares of the amplitude of points within the window. In other embodiments energy is computed as the sum of the absolute values of the amplitude. In some embodiments the energy contained in a low-frequency scale and a high-frequency scale is computed within the window and the ratio of the energy in the lower frequency scale and the higher frequency scale is compared to a threshold. In some embodiments, if the energy in the lower-frequency scale is more than about 2.5 times the energy in the higher-frequency scale, the detected ventricular depolarization is characterized as an ectopic beat (e.g., with energy concentrated mainly in the lower-frequency scale). In another embodiment, a statistical evaluation of ratios for beats in the series is performed to find an appropriate threshold for the energy ratio.

In some embodiments, the accuracy of AF detection can be improved by detecting the presence or absence of P-waves. In one embodiment, inter-beat intervals are evaluated, and if the evaluation indicates the presence of AF in the recording, the portion of the recording where AF has been detected is evaluated for the presence of P-waves. If P-waves are consistently found in that portion of the recording AF is considered absent.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., computing a time series of beat-to-beat intervals, denoising into subcomponents, computing an envelope and/or detecting the presence of AF). For example, in certain of the above-discussed embodiments, one or more modules are discrete logic circuits or programmable logic circuits configured and arranged for implementing these operations/activities, as in the circuit modules shown in FIG. 1. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., non-volatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, different thresholds may be used to achieve results applicable to specific embodiments and applications. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

The invention claimed is:

1. A method comprising:
computing a time series of inter-beat intervals from a recording of activity of a beating heart;
decomposing the time series into subcomponents;
computing an envelope of at least one of the subcomponents; and
detecting the presence of atrial fibrillation (AF) based upon characteristics of the envelope that are indicative of AF.

2. The method of claim 1, wherein detecting the presence of AF based upon characteristics of the envelope that are indicative of AF includes detecting the presence of AF based upon a comparison of the envelope to a first threshold indicative of AF.

3. The method of claim 1, wherein the recording of activity includes a recording of at least one of:
an electrocardiogram;
a ballistocardiogram;
heart sounds;
blood pressure;
blood flow in an artery; and
a photoplethysmography signal of body tissue.

4. The method of claim 1, wherein computing the time series of inter-beat intervals includes:
detecting a plethora of heart beats in the recording;
identifying invalid beats from the detected beats;
computing a raw sequence of inter-beat intervals from consecutive ones of the detected beats;
creating a cleaned sequence of inter-beat intervals by excluding intervals computed using ones of the beats identified as being invalid; and
resampling said cleaned sequence of inter-beat intervals to create an equispaced time series of inter-beat intervals.

5. The method of claim 4, wherein identifying invalid beats includes identifying invalid beats based on characteristics in the recording selected from the group of:
  ventricular arrhythmias;
  characteristics indicating that a signal detected as a beat is not a beat; and
  noise beyond a noise threshold.

6. The method of claim 4, wherein identifying invalid beats includes identifying ectopic beats by:
  decomposing the recording into subcomponents,
  detecting the presence of ventricular depolarizations in the subcomponents,
  establishing a window around each detected ventricular depolarization,
  computing the energy of high frequency and low-frequency subcomponents in each window,
  computing, for each window, the ratio of low frequency energy to high frequency energy, and
  detecting the presence of an ectopic beat in the window based upon the computed ratio.

7. The method of claim 6, wherein computing high frequency energy in the window includes:
  selecting one or more subcomponents corresponding to high frequency, and
  computing the high frequency energy using at least one of the sum of squares of the amplitude and the sum of the absolute values of the amplitude.

8. The method of claim 7, wherein computing low frequency energy in the window includes:
  selecting one or more subcomponents corresponding to low frequency, and
  computing low frequency energy using at least one of the sum of squares of the amplitude and the sum of the absolute values of the amplitude.

9. The method of claim 6, wherein computing low frequency energy in the window includes:
  selecting one or more subcomponents corresponding to low frequency, and
  computing low frequency energy using at least one of the sum of squares of the amplitude and the sum of the absolute values of the amplitude.

10. The method of claim 1, wherein computing the time series of inter-beat intervals includes:
  detecting a plethora of heart beats;
  identifying valid beats from the detected beats;
  computing a sequence of inter-beat intervals from a series of consecutive ones of the beats, with invalid ones of the beats being excluded from the series of consecutive ones of the beats; and
  resampling said sequence of inter-beat intervals to create an equispaced time series of inter-beat intervals.

11. The method of claim 1, wherein decomposing the time series into subcomponents includes applying one of the following:
  a discrete cosine transform;
  a stationary wavelet transform;
  a discrete wavelet transform;
  a filter bank;
  a synchrosqueezed wavelet transform;
  a Gabor transform;
  a short-term Fourier transform;
  a continuous wavelet transform; and
  a wavelet packet transform.

12. The method of claim 1, wherein the at least one of the subcomponents includes at least one subcomponent having a frequency corresponding to a highest frequency of the subcomponents.

13. The method of claim 1, wherein detecting the presence of AF includes detecting the presence of AF based upon the envelope exceeding a first threshold for a predetermined amount of time.

14. The method of claim 13, wherein detecting the presence of AF includes detecting the presence of AF based upon:
  the envelope exceeding the first threshold for the predetermined amount of time, and
  a computed metric of entropy exceeding an entropy threshold.

15. The method of claim 14, further including computing the metric of entropy for at least one of:
  the time series of inter-beat intervals;
  a subcomponent; and
  a product of subcomponents.

16. The method of claim 14, further including computing the metric of entropy using one of sample entropy and approximate entropy.

17. The method of claim 1, further including detecting an absence of AF based upon the envelope falling below a second threshold for a predetermined amount of time.

18. A method comprising:
  computing a time series of inter-beat intervals from a recording of activity of a beating heart, excluding intervals characterized by ectopic beats;
  decomposing the time series into subcomponents;
  computing an envelope of at least one of the subcomponents; and
  detecting the presence of atrial fibrillation (AF) based upon characteristics of the envelope that are indicative of AF.

19. The method of claim 18, wherein excluding intervals characterized by ectopic beats includes computing a raw sequence of inter-beat intervals from consecutive ones of detected beats in the recording, and creating a cleaned sequence of inter-beat intervals from the raw sequence of inter-beat intervals by excluding intervals computed using ones of the beats characterized as being ectopic.

20. The method of claim 18, wherein excluding intervals characterized by ectopic beats includes:
  decomposing the recording into subcomponents,
  detecting the presence of ventricular depolarizations in the subcomponents,
  establishing a window around each detected ventricular depolarization,
  computing the energy of high frequency and low-frequency subcomponents in each window, and
  detecting the presence of an ectopic beat in the window based upon a ratio of energy of the low frequency components to energy of the high frequency components being indicative of the ectopic beat.

21. The method of claim 18, wherein computing the time series of inter-beat intervals includes:
  detecting a plethora of heart beats in the recording;
  identifying invalid beats from the detected beats as beats exhibiting ectopic characteristics;
  computing a raw sequence of inter-beat intervals from consecutive ones of the detected beats;
  creating a cleaned sequence of inter-beat intervals by excluding intervals computed using ones of the beats identified as being invalid; and
  resampling said cleaned sequence of inter-beat intervals to create an equispaced time series of inter-beat intervals.

22. An apparatus comprising:
  an input port configured and arranged for receiving a signal indicative of activity of a beating heart; and
  a processing circuit configured and arranged with the input port to:
    compute a time series of inter-beat intervals from a recording of activity of the beating heart;
    decompose the time series into subcomponents;

compute an envelope of at least one of the subcomponents; and detect the presence of atrial fibrillation (AF) in the received signal based upon characteristics of the envelope that are indicative of AF.

23. The apparatus of claim 22, wherein the processing circuit is configured and arranged to compute the time series of inter-beat intervals by excluding intervals characterized by ectopic beats.

24. The apparatus of claim 23, wherein the processing circuit is configured and arranged to exclude intervals characterized by ectopic beats by
computing a raw sequence of inter-beat intervals from consecutive ones of detected beats in the recording, and
creating a cleaned sequence of inter-beat intervals from the raw sequence of inter-beat intervals by excluding intervals computed using ones of the beats characterized as being ectopic.

25. The apparatus of claim 23, wherein the processing circuit is configured and arranged to exclude intervals characterized by ectopic beats by:
decomposing the recording into subcomponents,
detecting the presence of ventricular depolarizations in the subcomponents,
establishing a window around each detected ventricular depolarization,
computing the energy of high frequency and low-frequency subcomponents in each window, and
detecting the presence of an ectopic beat in the window based upon a ratio of energy of the low frequency components to energy of the high frequency components being indicative of the ectopic beat.

26. The apparatus of claim 25, wherein the processing circuit is configured and arranged to
compute the high frequency energy in the window by selecting one or more subcomponents corresponding to high frequency, and computing the high frequency energy using at least one of the sum of squares of the amplitude and the sum of the absolute values of the amplitude, and
compute the low frequency energy in the window by selecting one or more subcomponents corresponding to low frequency, and computing the low frequency energy using at least one of the sum of squares of the amplitude and the sum of the absolute values of the amplitude.

27. The apparatus of claim 22, wherein the processing circuit is configured and arranged to compute the time series of inter-beat intervals by:

detecting a plethora of heart beats in the recording;
identifying invalid beats from the detected beats;
computing a raw sequence of inter-beat intervals from consecutive ones of the detected beats;
creating a cleaned sequence of inter-beat intervals by excluding intervals computed using ones of the beats identified as being invalid; and
resampling said cleaned sequence of inter-beat intervals to create an equispaced time series of inter-beat intervals.

28. The apparatus of claim 27, wherein the processing circuit is configured and arranged to identify the invalid beats based on characteristics in the recording selected from the group of:
ventricular arrhythmias;
characteristics indicating that a signal detected as a beat is not a beat; and
noise beyond a noise threshold.

29. The apparatus of claim 22, wherein the processing circuit is configured and arranged to compute the time series of inter-beat intervals by:
detecting a plethora of heart beats;
identifying valid beats from the detected beats;
computing a sequence of inter-beat intervals from a series of consecutive ones of the beats, with invalid ones of the beats being excluded from the series of consecutive ones of the beats; and
resampling said sequence of inter-beat intervals to create an equispaced time series of inter-beat intervals.

30. The apparatus of claim 22, wherein the processing circuit is configured and arranged to detect the presence of AF in response to:
the envelope exceeding a first threshold for a predetermined amount of time, and
a computed metric of entropy.

31. A method for detecting ectopic beats in an ECG recording, the method comprising:
decomposing the recording into subcomponents;
detecting the presence of ventricular depolarizations in the subcomponents;
computing the energy of high frequency and low-frequency ones of the subcomponents in respective time windows around each ventricular depolarization; and
detecting the presence of an ectopic beat in one of the time windows based upon a ratio of energy of the low frequency components to energy of the high frequency components being indicative of the ectopic beat.

* * * * *